United States Patent [19]

Kontturi et al.

[11] Patent Number: 5,637,084

[45] Date of Patent: Jun. 10, 1997

[54] ELECTROCHEMICAL METHOD AND DEVICE FOR DRUG DELIVERY

[76] Inventors: Kyösti E. A. Kontturi, Ylistörmä 5 A 2, Espoo, Finland, SF-02210; Lasse S. Murtomäki, Lähderanta 20 B 34, Espoo, Finland, SF-02720

[21] Appl. No.: 302,657

[22] PCT Filed: Mar. 10, 1993

[86] PCT No.: PCT/FI93/00083

§ 371 Date: Oct. 20, 1994

§ 102(e) Date: Oct. 20, 1994

[87] PCT Pub. No.: WO93/17755

PCT Pub. Date: Sep. 16, 1993

[30] Foreign Application Priority Data

Mar. 10, 1992 [GB] United Kingdom ............ 9205155

[51] Int. Cl.$^6$ ........................................ A61N 1/30
[52] U.S. Cl. ............... 604/20; 604/290; 424/449
[58] Field of Search ............... 604/20–21, 890.1, 604/892.1, 290; 429/2, 8, 105; 424/424, 449

[56] References Cited

U.S. PATENT DOCUMENTS

| | | |
|---|---|---|
| 542,459 | 7/1895 | Beckwith . |
| 868,123 | 10/1907 | Randall . |
| 4,171,409 | 10/1979 | Loeb .................... 429/17 |
| 4,722,726 | 2/1988 | Sanderson et al. . |
| 4,731,049 | 3/1988 | Parsi .................... 604/20 |

FOREIGN PATENT DOCUMENTS

| | | |
|---|---|---|
| 0316065 | 5/1989 | European Pat. Off. . |
| 0 369 945 | 5/1990 | European Pat. Off. . |
| 762259 | 4/1934 | France . |
| 410009 | 5/1934 | United Kingdom . |
| 87/04936 | 8/1987 | WIPO . |

OTHER PUBLICATIONS

Banga and Chien, "Iontophoretic Delivery of Drugs: Fundamentals, Developments and Biomedical Applications," *J. Controlled Release* 7:1–24 (1988).

Bannon et al., "Iontophoretically Induced Transdermal Delivery of Salbutamol," *Drug Devel. and Indust. Pharm.* 14(15–17):2151–2166 (1988).

Chien et al., "Direct Current Iontophoretic Transdermal Delivery of Peptide and Protein Drugs," *J. Pharm. Sci.* 78(5):376–383 (1989).

Singh and Roberts, "Transdermal Delivery of Drugs by Iontophoresis: A Review," *Drug Design and Delivery* 4:1–12 (1989).

Tyle, P., "Iontophoretic Devices for Drug Delivery," *Pharm. Res.* 3(6):318–326 (1986).

Wearley and Chien, "Enhancement of the in Vitro Skin Permeability of Azidothymidine (AZT) via Iontophoresis and Chemical Enhancer," *Pharm. Res.* 7(1):34–40 (1990).

Weinstein and Leitz, "Electric Power from Differences in Salinity: The Dialytic Battery," *Science* 191:557–559 (1976).

*Primary Examiner*—Mark Bockelman
*Attorney, Agent, or Firm*—Sterne, Kessler, Goldstein, & Fox P.L.L.C.

[57] ABSTRACT

An iontophoretic method for drug delivery may be powered by producing the necessary electropotential to deliver the drug using a difference in concentration of a salt across an anion selective membrane and a cation selective membrane; thereby creating an electropotential between the membranes.

20 Claims, 6 Drawing Sheets

ANION SELECTIVE MEMBRANE (A)

CATION SELECTIVE MEMBRANE (C)

ELECTROCHEMICAL METHOD AND DEVICE FOR DRUG DELIVERY

BACKGROUND OF THE INVENTION

This application is a 371 of PCT/FI 93/00083 filed Mar. 10, 1993.

The present invention relates to an iontophoretic method for drug delivery and a device suitable for use in carrying out this method.

In the present method, an electric current is generated by creating Galvani potential differences across at least two different ion selective membranes via a salt concentration difference over the membranes and bringing one artion selective membrane and one cation selective membrane into contact with human or animal body either directly or indirectly. According to a feature of the invention at least one reservoir containing a salt solution is needed, the concentration of which differs from the salt concentration of the extracellular fluids in human or animal tissues. The method of the invention can be specially used with transdermal preparations but also with mucoadhesive preparations and implants. For simplicity, the description which follows will refer to devices which are transdermal preparations, but it is to be understood that the method and device may be adapted to apply to mucoadhesive preparations and implants.

DESCRIPTION OF THE BACKGROUND ART

Iontophoresis or iontophoretic therapy is the delivery into human or animal tissue of a drug by the use of an electric field or current. Reviews of methods, devices and drugs suitable for iontophoretic delivery are contained in e.g. Journal of Controlled Release Vol. 7, 1988, pp. 1–24, Drug Design and Delivery Vol. 4, 1989, pp. 1–12 and Journal of Pharmaceutical Sciences Vol. 78, 1989, No. 5, pp. 376–383. In addition to transdermal applications the methods have also been used in ophthalmologic therapy (A. K. Banga & Y. W. Chien, *J. Controlled Release* Vol. 7, 1988, pp. 1–24).

U.S. Pat. No. 4,722,726 discloses a device for iontophoretic delivery of active ingredients, where an ion selective membrane is used to only separate an electrode and a first chamber containing an electrolyte from a second chamber containing an active ingredient. An additional power source for the genereetion of electric current is needed.

For the generation of electric current some kind of a battery is always needed, and current is introduced into the tissues of the body via wires and electrodes. The electric circuit is closed through the body of a patient after attaching a device on the surface of the body or by the implantation of a device. The flux of a drug is enhanced mainly due to the migration of ionized drug molecules but also secondary effects e.g. electroosmotic convective flow and tissue alteration due to current can be responsible for the flux enhancement. Due to these secondary effects also the flux of neutral drug molecules is enhanced in the presence of electric field (L. Wearley & Y. W. Chien, *Pharmaceutical Research* Vol. 7, 1990, pp. 34–40).

When current is passing in the circuit electrochemical reactions take place at the electrodes, and possibly harmful reaction products can be generated or useful compounds consumed at the electrodes. Such a reaction is usually the splitting of water which results in the change of pH and in the need to buffer the solutions (see e.g. EP 369945). Iontophoretic burns, skin irritation and electric shocks have been reported (P. Tyle, Pharmaceutical Research, Vol. 3, No. 6, 1986, pp. 318–326 and A. K. Banga & Y. W. Chien, *Journal of Controlled Release*, Vol. 7, 1988, pp. 1–24).

SUMMARY OF THE INVENTION

The present invention provides an iontophoretic device in which the power to generate the necessary electropotential to deliver the drug is provided by a difference in concentration of a salt across an anion selective membrane and a cation selective membrane. There is no need for a conventional battery or any electrodes. The present invention therefore provides a method of administering a drug, which is ionized or ionizable in situ, to a human or animal body which method comprises forming a circuit by placing in electrolytic contact:

(i) the body and (ii) one or more electrolyte solutions of which at least one is contained in a compartment, having a boundary which comprises a membrane selective to cations and a membrane selective to anions, the concentration of electrolyte in the compartment(s) being such that on formation of the circuit ions move through the ion selective membranes; the drug being present, at least initially, in one or more of said solutions such that the movement of ions causes movement of the drug in ionized form into the body.

The present invention also provides a drug delivery device comprising a compartment containing:

i) a drug which is in ionized form or ionizable in situ; and ii) an electrolyte solution of a concentration higher than the concentration of electrolyte in extracellular fluids in human or animal tissue said compartment having a boundary which comprises a membrane which selectively allows cations to pass through and a membrane which selectively allows anions to pass through.

An alternative device is one which comprises at least three compartments 1,2 and 3, each containing an electrolyte solution and in which:

i) compartment 1 contains a solution of different concentration from the solutions of compartments 2 and 3, 1 being in electrolytic contact with 2 via a membrane C which selectively allows cations to pass through, and in electrolytic contact with reservoir 3 via a membrane A which selectively allows anions to pass through;

ii) at least one of 2 and 3 further contains a drug which is in ionized form or capable of being ionized in situ;

iii) 2 and 3 each have as part of their boundaries a membrane M that is permeable to electrolyte ions and, if present, drug;

said device being capable of forming a circuit when brought into contact with a human or animal body, the concentrations of electrolyte solutions being such that on formation of the circuit ions move through membranes A and C causing the drug in ionized form to move into the body.

The drug administered by the device is ionized or ionizable in situ, i.e. it is capable of existing in ionized form under the conditions in which the device is used. It is also possible that the drug may be capable of associating with an ionic species during use of the device.

BRIEF DESCRIPTION OF THE DRAWINGS

In the following description of the invention reference is made to the figures of the drawings.

DESCRIPTION OF THE PREFERRED EMBODIMENTS

When two salt solutions I and II of different concentrations are separated by an ideal ion selective membrane which allows only one of the ions, with a charge number $z_i$, to cross the membrane but excludes all the other ions, a Galvani potential difference, $\Delta\Phi$, across the membrane is created, and it is given by Equation (1)

$$\Delta\Phi = \frac{RT}{z_i F} \ln \frac{a_i(I)}{a_i(II)} \quad (1)$$

where $a_i(I)$ and $a_i(II)$ are the activities of the ion in the solutions I and II, $R=8.314$ J K$^{-1}$ mol$^{-1}$, $F=96487$ As mol$^{-1}$ and T is the thermodynamic temperature (K). However, the ion cannot cross the membrane because of the electroneutrality condition $\Sigma z_i \cdot c_i = 0$ wherein $c_i$ is concentration, but if electrodes which are reversible with respect to any of the ions are placed in the solutions and connected with each other, ions begin to flow through the membrane because electrode reactions equilibrate the loss and the excess of the ion. This phenomenon is known in concentration cells with transference and ion selective membranes.

Figure 1:
FIG. 1 shows the principle of the invention.
Figure 1:
Figure 1:
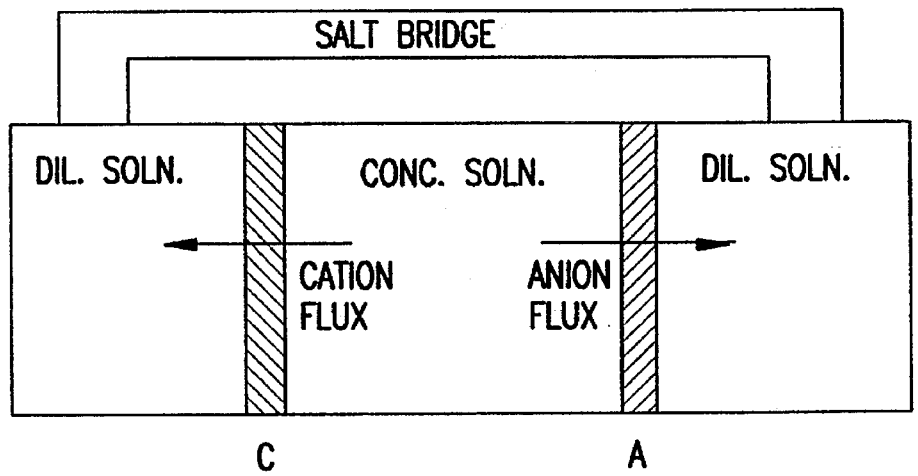

When a concentrated salt solution is separated from two dilute solutions with two different ion selective membranes and the dilute solutions are connected via a salt bridge with the same dilute concentration as presented in FIG. 1., ion fluxes i.e. electric current can be obtained because the removal of an equivalent of cations is balanced with the corresponding removal of anions. If the salt bridge is replaced by reversible electrodes which are in contact, the process known as reverse electrodialysis is obtained (J. N. Weinstein & F. B. Leitz, Science, Vol. 191, pp. 557–559 and U.S. Pat. No. 4171409). Human or animal body can be considered to form the salt bridge and thus an iontophoretic method for drug delivery is obtained. No electrodes or conventional batteries are needed to generate current.

The drug is placed in the appropriate dilute salt solution according to the drug's electric charge: positively charged drugs are placed in solution that is separated from the reservoir by a cation selective membrane and negatively charged drugs in the solution that is separated by an anion selective membrane.

The magnitude of current generated can be calculated by Ohm's law $I=\Delta\Phi/R_c$, where $R_c$ is the resistance of the half-circuit. The flux of a drug, $J_D$, in this case with a perfect sink condition is approximately given by Equation (2)

$$J_D = D_D \frac{c_D}{h} \frac{v}{1-e^{-v}} \; ; v = \frac{z_D F I R \Omega}{RT} \quad (2)$$

where $c_D$ is the concentration of a drug in the reservoir, $D_D$ is the integral diffusion coefficient of a drug in the tissue which limits the flux, and h and $R_\Omega$ are the thickness and resistance of that tissue. The limiting value $Z_D=0$ for electrically neutral drugs yields the passive flux $J_{D,p}=D_D \cdot c_D/h$.

Suitable drugs for the method of the invention are those which have electric charge in water solution. It is therefore particularly suitable for the delivery of ionized drugs. Neutral drugs such as peptides may be delivered using this method by causing the drug to ionize e.g. by selecting an appropriate pH of the drug solution.

The present method may be used for delivering any drug capable of being ionized and which is appropriate for iontophoretic administration. Such drugs include local anaesthetics e.g. lignocaine and lidocaine; antibiotics and antibacterials e.g. streptomycin and penicillin; peptides and proteins, such as insulin; vasodilators; steroids; beta-blockers, such as metoprolol, sotalol and propranolol; and other drugs such as papaverine. Further drugs are listed in the reviews of iontophoretic techniques mentioned earlier. It is possible to deliver more than one drug at the same time.

The maximum salt concentration of the concentrated solution is due to the solubility of the salt. The lowest limit of the concentration of the dilute solution is that the solution must be capable of conducting current. The salt concentration in the dilute solution can also be less than that in the extracellular fluids of human or animal tissues. All pharmaceutically acceptable salts can be used. Typical salts include e.g. NaCl and KCl.

The ion selective membranes can be of any of the commercial types available, such as Ionics (Ionics, USA), Nation (a perfluorosulfonic acid membrane of DuPont Limited), Neosepta (Tokoyama Soda Limited), Tosflex (Tasoh Corporation), Ionac (Sybron Chemicals) and Selemion (Asahi Glass).

The device for carrying out the method of the present invention can be of several different types of design. The following types of design presented are not by any means limiting but only illustrative. FIG. 1, which shows the principle of the invention, presents a three compartment design where a reservoir of the concentrated salt solution is placed between the two reservoirs of dilute salt solution with different ion selective membranes, and the drug is added in the appropriate one of the dilute solutions depending on the charge of the drug. A very dilute solution can also be placed between two concentrated solutions maintaining the design otherwise the same. In this case the drug is placed in the concentrated solution appropriate to the charge on the drug. Now greater potential differences can be obtained but at the same time the resistance of the circuit increases. Both designs described above have the similarity that drug is not passed through the ion selective membranes.

Figure 2:
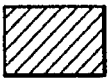
FIG. 2 shows an example of a one compartment design of the device.
Figure 2:
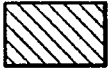
Figure 2:
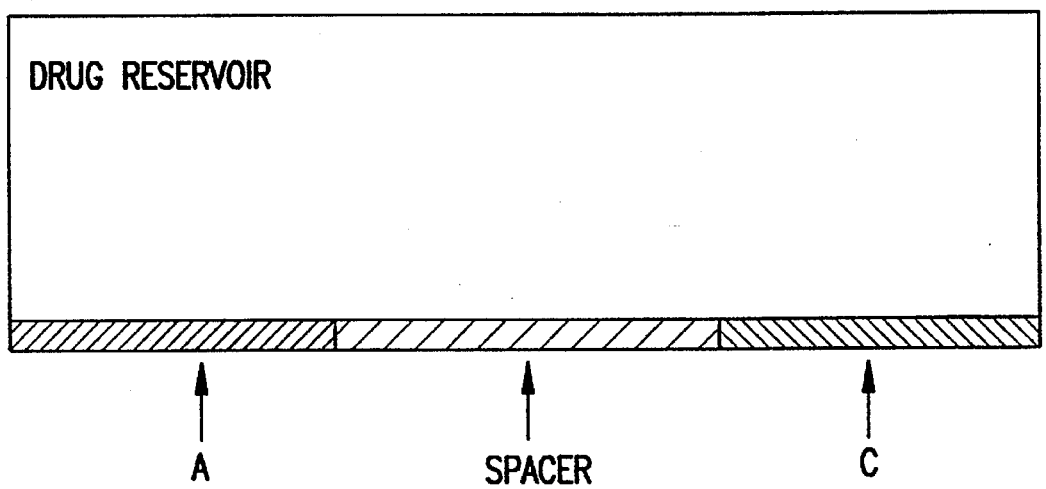

In a one compartment design there is only one reservoir. This reservoir contains both salt solution and drug as illustrated in FIG. 2, and the tissues of a body itself provides the other compartments. The solution in the device should in this embodiment be more concentrated than the salt concentration of extra cellular fluids of human or animal tissues. In this case drug has to transfer through one of the ion selective membranes, depending on this charge, and this may lead to use of tailor-made membranes in order to allow the passage of drug molecules with great size.

Figure 3:
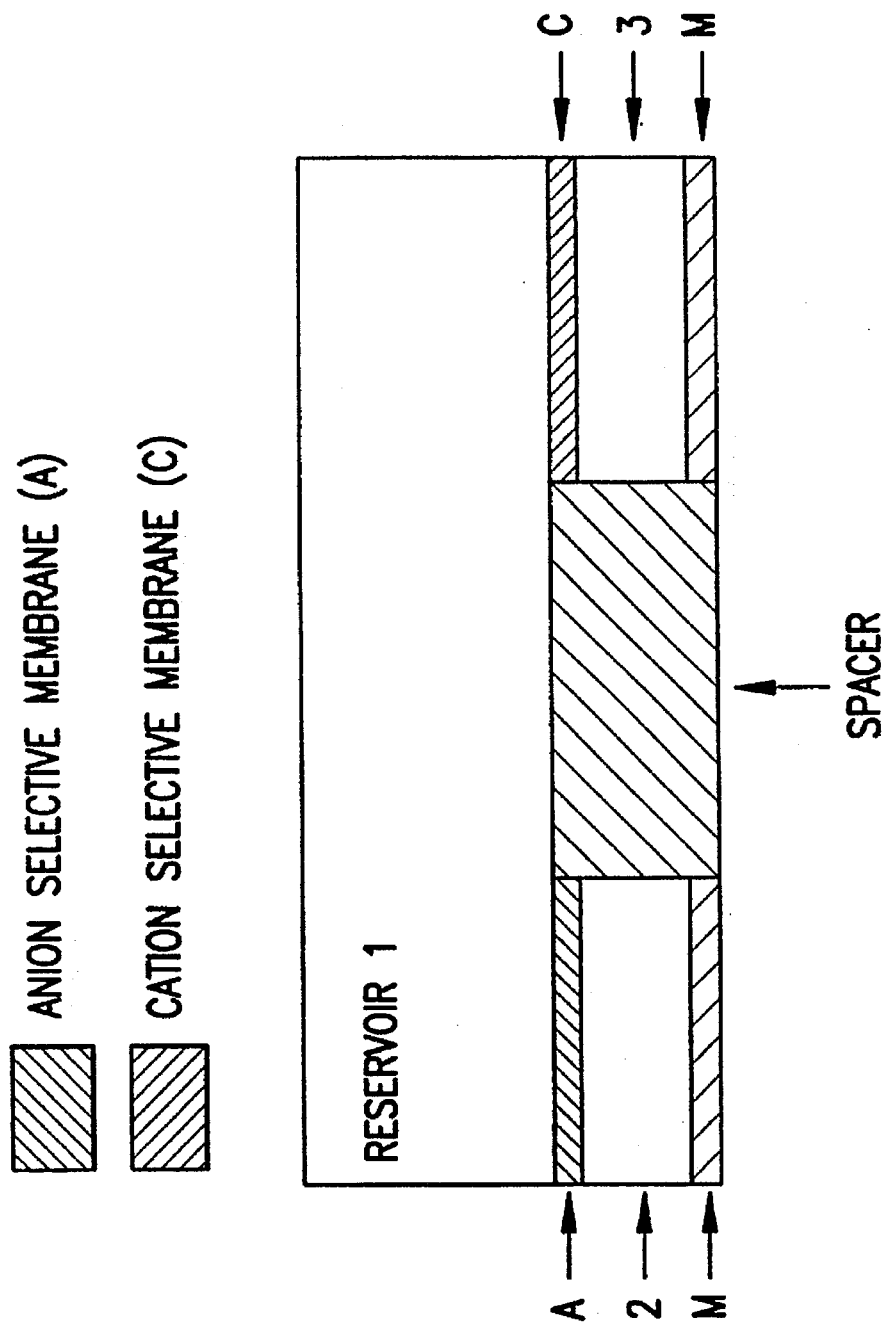
FIG. 3 shows an embodiment of a device.

An example of a practical embodiment of the device is illustrated in FIG. 3. For example, the body of the device may be formed of a silicon material e.g. Silastic and the ion-selective membranes may be e.g. Neosepta and Tosflex. The device comprises a reservoir 1 connected to a reservoir 2 by an anion selective membrane A, and connected to a cation selective membrane C, the reservoir 2 and membrane A being separated from the reservoir 3 and membrane C by a spacer S which is non-porous to the solutions being used. The membrane M borders reservoirs 2 and 3 and is intended to make contact with the body to be treated.

The reservoir 1 may contain a concentrated salt solution and the reservoirs 2 and 3 may contain dilute salt solutions or vice versa; preferably the reservoir 1 contains a concentrated salt solution. The drug is placed in either of the reservoirs 2 or 3 depending on its charge. The drug may also be placed in the reservoir 1, but in this case the drug has to penetrate also one of the ion selective membranes as described before. The membrane M depicted below the reservoirs 2 and 3 may be an ordinary membrane which allows the penetration of the drug and the salt ions. It is intended that the reservoirs 2 and 3 be brought into contact with the human or animal body via that membrane. A spacer separates the ion selective membranes from each other. The spacer may be for instance an empty space or an impermeable wall.

Figure 4:
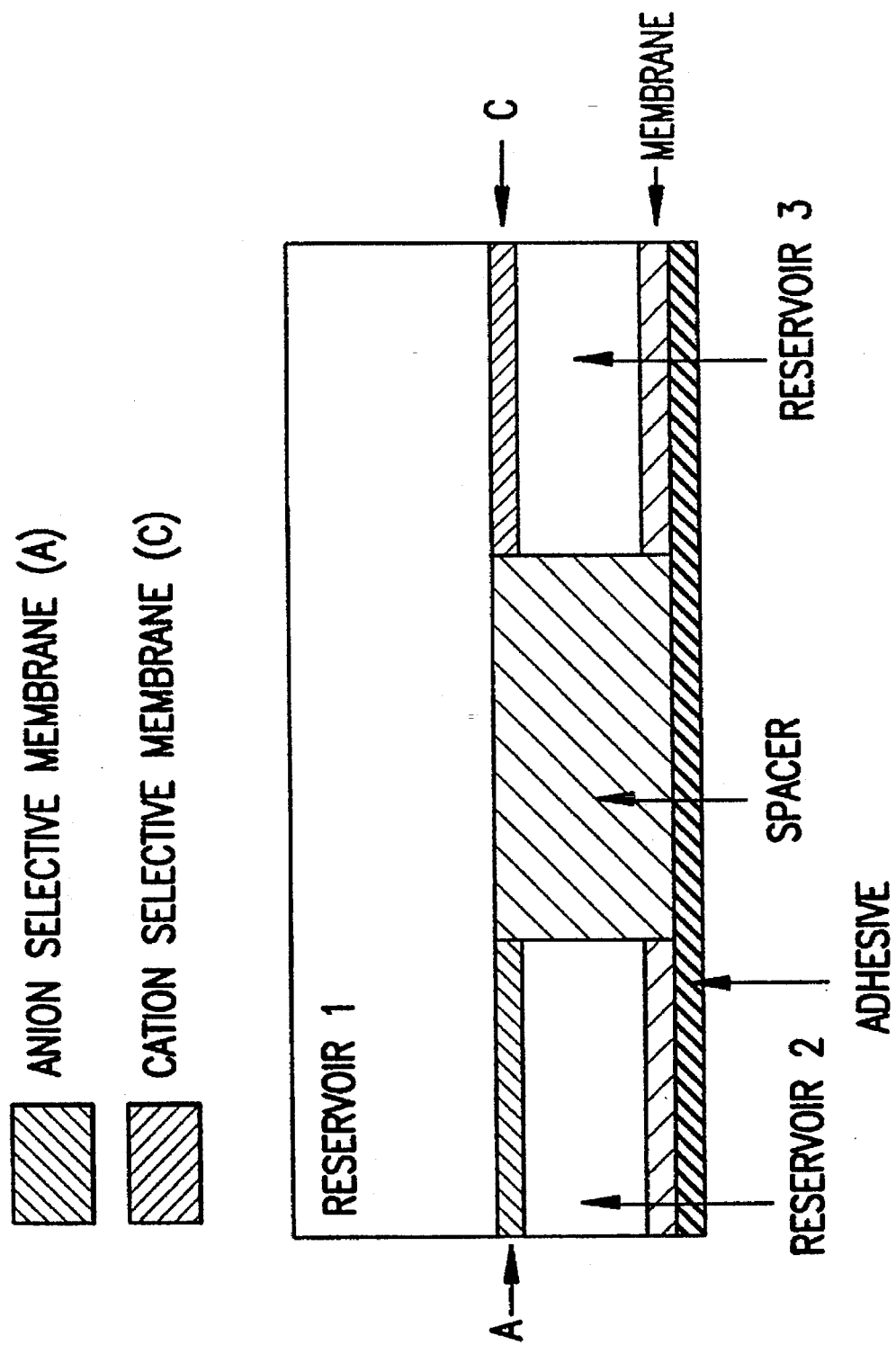
FIG. 4 shows an embodiment of a device for transdermal therapy.

For transdermal therapy the device may have an adhesive layer as illustrated in FIG. 4, which further may be covered by a tape. After the covering tape is removed the device is attached to the skin. The adhesive layer may contain one or more penetration enhancers to reduce the resistance of the skin. The salt solutions may be immobilized in a hydrogel, such as agar-agar or agarose, since it has been noticed that the transport properties of ions are reduced surprisingly little in such a gel (Y.B. Bannon et al., *Drug Development and Industrial Pharmacy*, Vol. 14, No. 15–17, 1988, pp. 2151–2166).

A wide range of salt concentrations may be used in a device, e.g. concentrations from 0.005M to 5M. Typically a difference in initial concentrations in two adjacent reservoirs separated by an ion-selective membrane will be 60 to 130 fold, preferably about 100 fold e.g. 0.01M and 1M NaCl or 0.05M and 5M NaCl. This can be expected to produce a potential difference of 120 mV over the ion-selective membranes.

The life-time of the device is determined by the concentrations of the salt solutions and can be calculated from the Faraday's law as follows:

$$\frac{dn}{dt} = \frac{I}{z_i F} \rightarrow \Delta t = \frac{z_i F \Delta n}{I} \quad (3)$$

where $\Delta t$ is the time used, $\Delta n$ is the amount of salt consumed (mol) and I, $z_i$ and F are as defined before.

Figure 5:
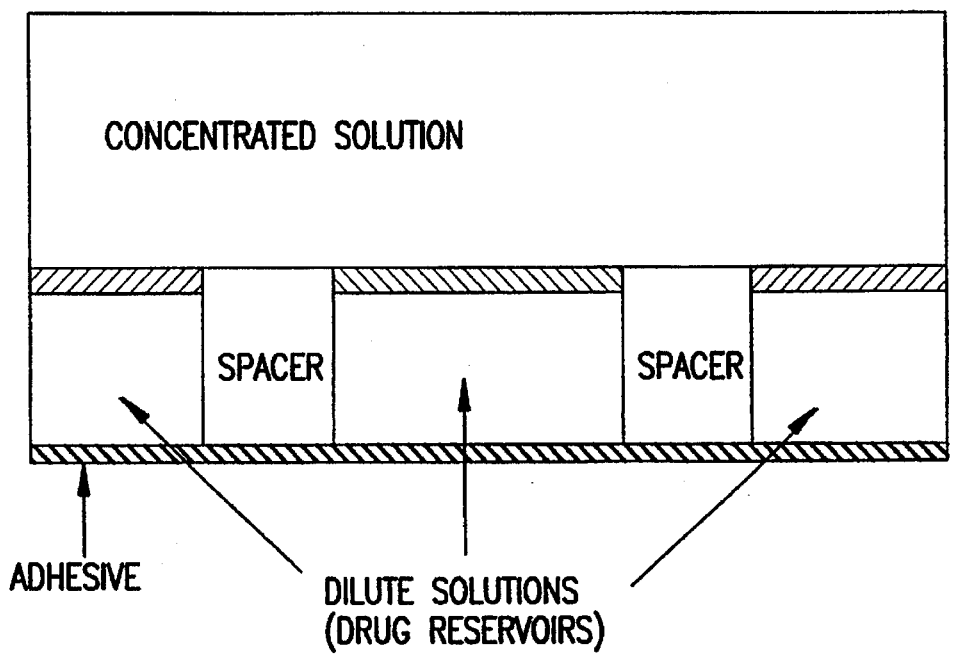
FIG. 5 shows a side-view of an embodiment of a circular device for transdermal therapy.
Figure 6:
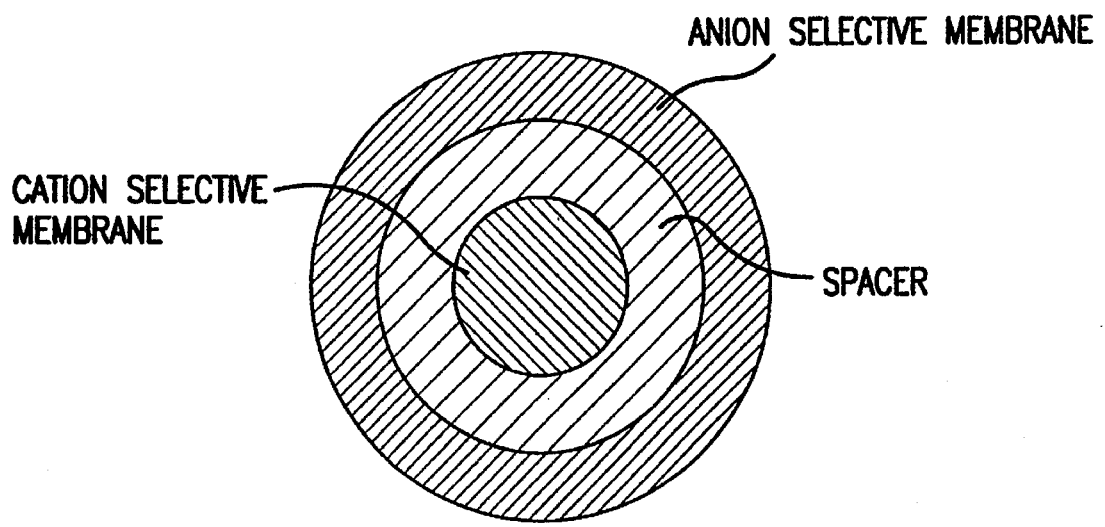
FIG. 6 shows a bottom-view of an embodiment of a circular device for transdermal therapy.

The life-time of the device is also dependent on the volume of the salt solutions because the transfer of ions tends to equalize, though slowly, the concentrations. The power of the device is determined by the area and ideality of the membranes: the greater these quantities are the greater is the current. A circular, concentric form is an example of a device in which a long life time and high current are combined. A side-view and a bottom-view of an embodiment of a circular device are presented in FIG. 5 and FIG. 6, respectively.

Figure 7:
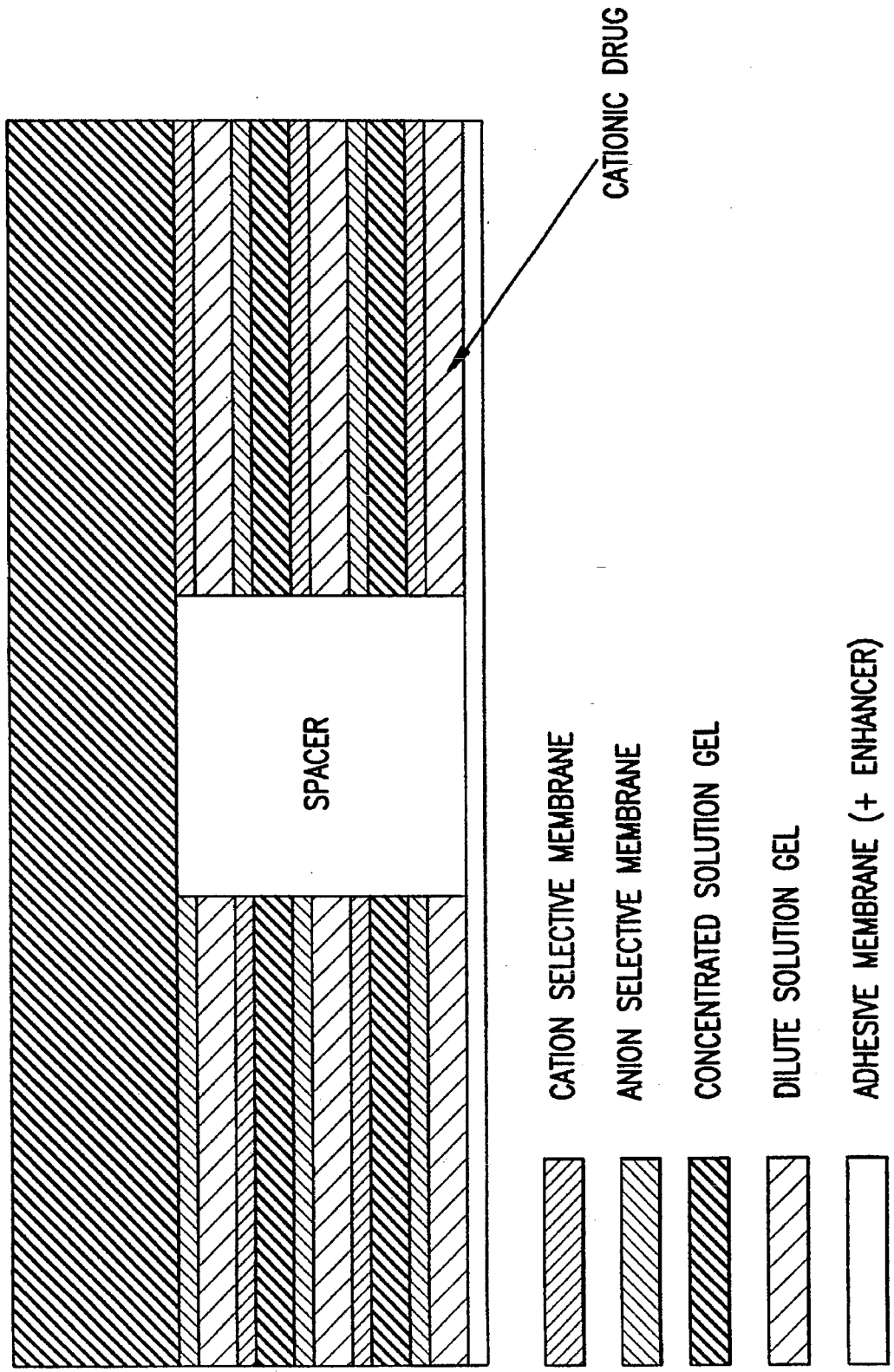
FIG. 7 shows an embodiment of a device which comprises alternating dilute and concentrated salt solutions and anion and cation selective membranes.

The electric potential supplied by the salt concentration difference across membranes in a single cell device e.g. as shown in FIG. 1, is lower than the electric potential which may be obtained from conventional batteries. However, the unit presented in FIG. 1 may be connected in series to provide a higher potential and greater current. Reservoirs of dilute and concentrated solutions and anion selective and cation selective membranes alternate and a drug to be administered is in one of the outer reservoirs. An example of that kind of a device is presented in FIG. 7. The outer reservoirs are brought into contact with human or animal body via a membrane that is permeable to the drug and salt ions. If the salt concentrations between adjacent reservoirs would result in a potential difference of 120 mV in a single cell, connection of four units in series will produce a potential difference of 500 mV.

Figure 8:
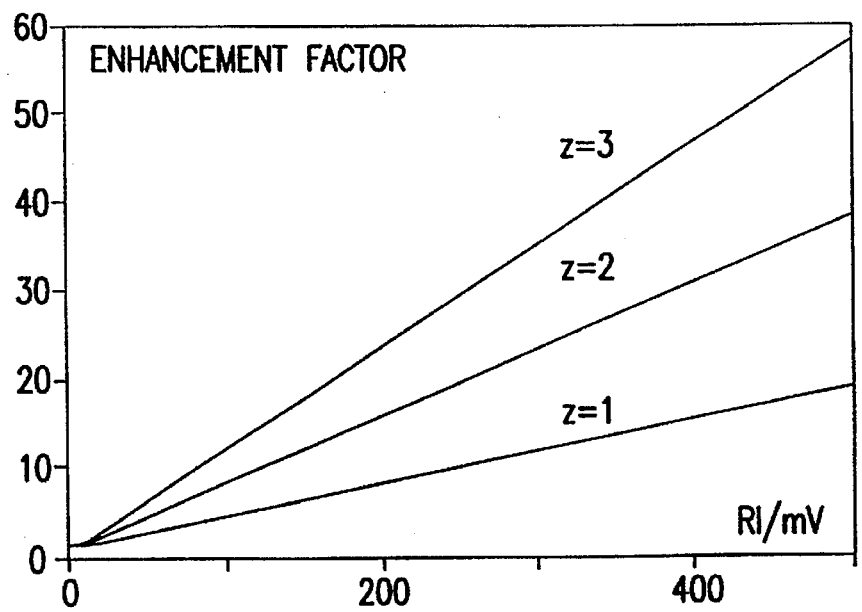
FIG. 8 shows graphic presentation of the equation 2.

Referring to equation 2, the term $v/(1-e^{-v})$ may be regarded as an enhancement factor, which indicates how the flux of a drug varies with the electric potential and the charge on the drug ion. This relationship is shown in FIG. 8 for ionic charges (z) of ±1, ±2 and ±3. For example when the drug ion has a charge of ±1, an electric potential of 500 mV results in a 20-fold increase in the drug flux compared with the passive flux.

The examples of devices presented in FIGS. 4 to 7 are designed specially for transdermal purposes but they can easily be modified for other purposes, such as mucoadhesive purposes, for example, where the resistance of the flux limiting tissue is much less than that of skin which results in greater currents.

The iontophoretic method of the present invention has several advantages. In the absence of electrodes no reactions take place and the changes in composition or pH of the solutions and degradation of drug are avoided. The absence of a battery and electrodes removes the need for safety precautions and problems with disposal of the device. Furthermore, ordinary commercial membranes and salts can be utilized which means low costs. Since the current produced is relatively low, there is the further advantage that adjusting the current to avoid skin irritation is not required. From Faraday's law it can be calculated that changes of the concentrations due to current are negligible for several weeks. The device may therefore be used to administer the drug over a long time.

Experiment 1

The principle of the method was experimentally verified using a reverse electrodialysis set up: a 1.5 mol dm$^{-3}$ NaCl solution was separated with Ionics 103-PZL-389 anion exchange and Nafion 423 cation exchange membrane from 0.15 mol dm$^{-3}$ NaCl solutions which mimic the salt content of the blood circulation; snake skin preparates (*Elaphe obsoleta*) with 1,0 cm$^2$ area to mimic human *stratum corneum* were placed between membranes and Ag/AgCl electrodes, and current was monitored between the electrodes.

The device was able to maintain a current of 5–10 FA for several days which ensures the validity of Equation 1 and proves that the current was limited by the resistance of snake skin. It has been noticed in separate measurements that the resistance of snake skin with 1,0 cm$^2$ area varies between ca. 5 k$\Omega$ and 20 k$\Omega$ according to its hydration. It must be noticed that both membranes create approximately the same potential difference which has to overcome the resistance in its own branch of the circuit only. Also, it must be emphasized that the use of electrodes for the monitoring of current increases the entropy production of the system, and a device without electrodes is capable of maintaining higher current.

Experiment 2

Figure 9:
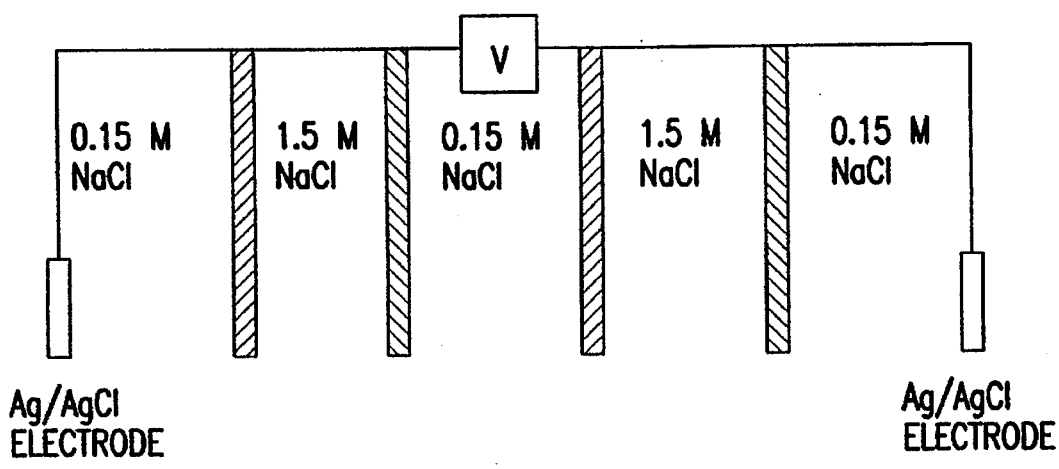
FIG. 9 shows the principle of a device used in Experiment 2.

The principle of a device which comprises alternating dilute and concentrated salt solutions and anion and cation selective membranes was tested using the system depicted in FIG. 9.

A indicates an Ionics 103-PZL-389 anion exchange membrane and C indicates a Nafion 423 cation exchange membrane.

The test revealed that the potential difference achieved from this system was twice as great as the potential difference achieved when only two ion selective membranes were used.

We claim:

1. A drug delivery device comprising:
   a) a single reservoir having an upper face and a lower face, wherein said lower face comprises a cation selective membrane (C), wherein said cation selective membrane is permeable to a cationic drug, and an anion selective membrane (A), wherein said anion selective membrane is permeable to an anionic drug;

b) an electrolyte solution having ions within said reservoir, wherein the ions in said electrolyte solution are also present in the human or animal tissue that will be in contact with said lower face of said reservoir, and wherein the concentration of said electrolyte solution is higher than the concentration of said electrolyte in said human or animal tissue; and c) at least one drug in said electrolyte solution, said drug being in ionized form at the pH of said electrolyte solution, wherein said concentration of said electrolyte solution is such that on contact of said lower face of said reservoir with said human or animal tissue, said drug and the ions in said electrolyte solution move through at least one of said selective membranes, causing said drug to be delivered to said tissue.

2. The device according to claim 1, wherein only one said drug is present, said drug being in the form of a salt, and the cation of said salt being pharmacologically active.

3. The device according to claim 1, wherein only one said drug is present, said drug being in the form of a salt, and the anion of said salt being pharmacologically active.

4. The device according to claim 1, wherein more than one said drug is present.

5. A method for delivering a drug comprising:

a) contacting said human or animal tissue with a device as defined in claim 1; and b) allowing said drug to be delivered to said tissue.

6. A drug delivery device comprising first, second, and third reservoirs, each of said reservoirs having an upper face and a lower face, and each of said reservoirs containing an electrolyte solution, having ions wherein a) said first reservoir contains an electrolyte solution of different concentration than said electrolyte solutions of said second and third reservoirs, said lower face of said first reservoir being in electrolytic contact with said upper face of said second reservoir via an anion selective membrane (A) and in electrolytic contact with said upper face of said third reservoir via a cation selective membrane (C);

b) at least one of said second and third reservoirs further contains a drug in ionized form at the pH of said electrolyte solutions in which said drug is contained;

c) said second and third reservoirs each have as part of their lower face a membrane (M), said membrane (M) being permeable both to the ions in said electrolyte solutions and to said drug; and d) said concentrations of said electrolyte solutions are such that on contact of said membrane (M) with human or animal tissue, said electrolyte solution ions move through said cationic and anionic selective membranes causing said drug to move through said reservoir lower face membrane (M) whereby said drug is delivered to said tissue.

7. The device according to claim 6, wherein said electrolyte solution in said first reservoir is more concentrated than said electrolyte solution in said second and third reservoirs.

8. The device according to claim 7, wherein said drug is a cation and wherein said concentration of said electrolyte solutions in each of said second and third reservoirs is at least as great as the electrolyte concentration in said tissue with which said membrane (M) is to be placed in contact.

9. The device according to claim 7, wherein said drug is a cation and wherein said concentrations of said electrolyte solutions in each of said second and third reservoirs is less than said electrolyte concentration in said tissue with which said membrane (M) is to be placed in contact.

10. The device according to claim 7, wherein said drug is an anion and wherein said concentration of said electrolyte solutions in each of said second and third reservoirs is at least as great as the electrolyte concentration in said tissue with which said membrane (M) is to be placed in contact.

11. The device according to claim 7, wherein said drug is an anion and wherein said concentration of said electrolyte solutions in each of said second and third reservoirs is less than the electrolyte concentration in said tissue with which said membrane (M) is to be placed in contact.

12. The device according to claim 6, wherein said electrolyte solution in said first reservoir is less concentrated than said electrolyte solutions in said second and third reservoirs.

13. The device according to claim 6, wherein said device is circular, and wherein said ion selective membranes (A) and (C) are concentric rings or.

14. The device according to claim 6, wherein said drag in said second reservoir is in the form of a salt, the anion of said salt being pharmacologically active.

15. The device according to claim 6, wherein said drug in said third reservoir is in the form of a salt, the cation of said salt being pharmacologically active.

16. A method for delivering a drug comprising:

a) contacting said human or animal tissue with a device as defined in claim 6; and b) allowing said drug to be delivered into said tissue.

17. A drug delivery device comprising at least four reservoirs connected in series and separated alternately by cation selective membranes (C) and anion selective membranes (A), wherein a) the first and last of said reservoirs are outer reservoirs:

b) each of said at least four reservoirs contains an electrolyte solutions having ions;

c) the concentrations of said electrolyte solutions in adjacent reservoirs alternate between higher and lower;

d) said outer reservoir containing said lower concentration of said electrolyte solution further contains a drug in ionized form at the pH of said electrolyte solution in said outer reservoir containing said lower concentration of said electrolyte solution;

e) said outer reservoir containing said drug has as part of boundary, in addition to said ion selective membrane, a membrane (M), said membrane (M) being permeable both to ions in said electrolyte solution and to said drug; and f) said concentrations of said electrolyte solutions are such that on contact with human or animal tissue, said ions move through said selective membranes (C) and (A), causing said drug to move through said membrane (M) and to be delivered to said tissue.

18. The device according to claim 17, wherein said drug is in the form of a salt, the cation of said salt being pharmacologically active, and said reservoir containing said drug being in contact with an adjacent reservoir via a cation selective membrane.

19. The device according to claim 17, wherein said drug is in the form of a salt, the anion of said salt being pharmacologically active, and said reservoir containing the drug being in contact with said an adjacent reservoir via an anion selective membrane.

20. A method for delivering a drug comprising:

a) contacting said human or animal tissue with a device as defined in claim 17; and b) allowing said drug to be delivered into said tissue.

* * * * *